March 11, 1958 W. E. SILVA Plant Pat. 1,690

ROSE PLANT

Filed June 26, 1957

WITNESS

Addison E. Avery

INVENTOR

WILLIAM E. SILVA by Rummler & Snow

ATTYS.

United States Patent Office

Plant Pat. 1,690
Patented Mar. 11, 1958

1,690

ROSE PLANT

William E. Silva, Sebastopol, Calif., assignor to Peter J. Booy Rose Nursery, San Jacinto, Calif., a partnership consisting of Peter J. Booy and Henry F. Eckardt Application June 26, 1957, Serial No. 668,275

1 Claim. (Cl. 47—61)

Figures 1, 2, 3:
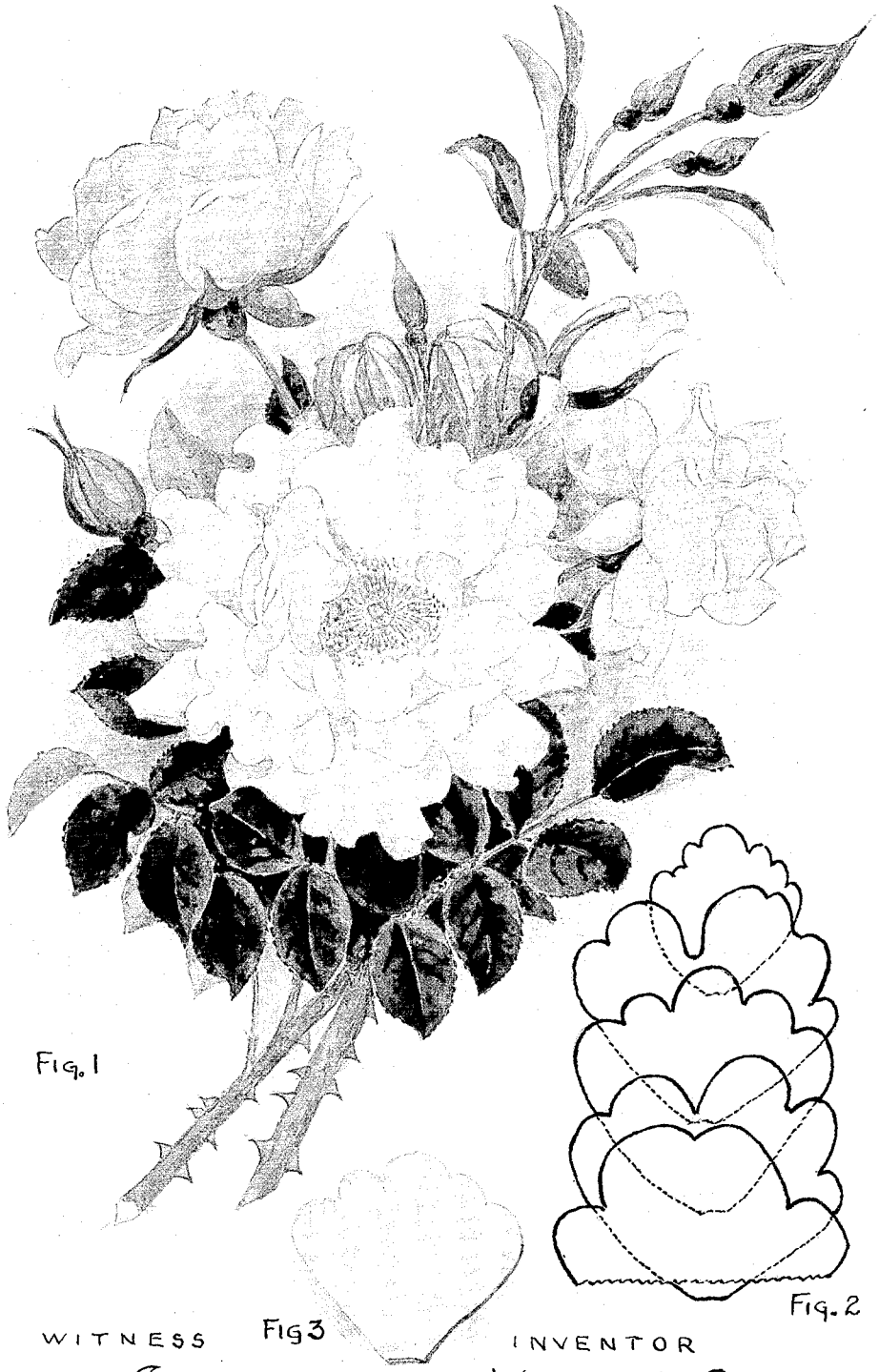

The new variety of rose plant herein described and illustrated is a cross between Henry Guillot (Plant Patent No. 337) and Mrs. Sam McGredy (unpatented), which was made in 1948 at Sebastopol, California. This new variety has been reproduced by me by cuttings, budding and grafting at Sebastopol, California, through several generations, and its characteristics appear to be permanently fixed.

The main object of this invention was to obtain a new rose which would possess certain desired characteristics of the parent varieties and constitute a marked improvement in the progeny, and these characteristics have been maintained by asexual propagation.

The distinctive features of this new variety are its early, continuous, long-season blooming habit; its lavish display of the rich, soft pink coloring of the flowers; prolific quantity of blooms; the unique undulating margins of the petals which enhance the pleasing appearance of the blooms; the very good lasting quality of the blooms; its freedom from disease; and its sturdy flower and leaf stalks. Its branching stalks are of adequate strength to support the profuse quantity of flowers.

In the accompanying painting the new rose is shown in Figure 1 in its natural colors. The pen and ink sketch of Fig. 2 illustrates the unusual scalloped margins of the petals several of which are shown in overlapped or shingled relation from the larger outermost to the smallest or innermost petal; and the sketch of Fig. 3 shows one of the petals to illustrate the base to tip coloring thereof.

The following is a detailed description of my new variety:

Parentage: Seedling.
*Seed parent.*—Henry Guillot (Pat. No. 337).
*Pollen parent.*—Mrs. Sam McGredy (unpatented).
Classification: Botanic, Grandiflora.

*Flower*

Blooming habit: Continuous. Early spring, midseason, and fall. Blooms profusely and is a very showy flower.
Size: Medium; 3½ inches.
Borne: Some singly and some in cluster.
Shape: When first opens, cup-shaped.
Petalage: 16–20 petals.
*Form.*—Varyingly undulated and somewhat serrated top margins.
*Color.*—Outer petals—coral-salmon. Inside petals—dark coral-salmon. Reverse side—light coral-salmon. Base—light yellow. No discoloration as flower ages.
Texture: Leathery.
Appearance: Velvety. Not much affected by hot or wet weather. Disease resistant to mildew, blackspot, rust, and usual rose plant diseases.
Fragrance: Medium.
Lasting quality:
*On plant.*—Good.
*As a cut flower.*—Good.

*Bud*

Size: 1 inch.
Form: Long and pointed, ovid shaped.
Color:
*When sepals first divide.*—American vermilion.
*When petals begin to unfurl.*—Salmon.
Sepals: Hooded over bud. Curl back when opening. Spear-shaped. Fall off as flower opens full.
Calyx:
*Shape.*—Funnel.
*Size.*—Large.
*Aspect.*—Smooth. Does not split and is not hairy or glandular.
Peduncle: Length, 16–18 inches. Not hairy.

*Plant*

Form: Bush.
Height: About 4 feet. Vigorous growth; branching.
Foliage: Medium quantity.
*Size of leaf.*—3 inches.
*Texture.*—Smooth.
*Color.*—Upper side—medium green. Under side—light green.
*Shape.*—Dentate.
*Petioles.*—Length—2¼ inches.
Prickles:
*Color.*—Reddish-brown.
*Size.*—3/16 inches.

*Genital organs*

Stamens, anthers:
*Length.*—27/64" and smaller.
*Number.*—130–140.
*Color.*—Red base—yellow above base.
*Arrangement.*—Clustered and cupped inward to form a complete circle.
*Pollen.*—Present and fertile. Color—yellow.
Styles: Number, 64–72. Length, 5/16 inch.
Ovaries: 64–72.
Fruit: Fertile; round in shape. Color at maturity—yellow.

The color designations according to "A Dictionary of Color by Maerz and Paul" are as follows:

| Part | Plate | Letter | No. |
|---|---|---|---|
| Flower: | | | |
| Base of petal (Yellow) | 9 | L | 1 |
| Lightest shade of pink on face of petal | 1 | D to G | 1 |
| Back of petals | 1 | A | 5 |
| Some shading into | 1 | A | 6 |
| Others shading into | 1 | H to K | 5 |
| Pistil or stamen tips | 12 | L | 9 |
| Leaves: | | | |
| Face of leaf | 22 | L | 9 |
| Back of leaf | 20 | J | 6 |
| Stems | 7 | C | 10 |
| Thorns | 7 | L | 4 |

The only variety comparable to this new variety of rose is its seed parent Henry Guillot; but the two are distinctively different, as my new variety is always in bloom and its pink color is entirely different. The new plant is winter hard and has a more pleasing coloring and a greater abundance of flowers than other plants of this kind. The marginal edges of the petals are uniquely scalloped, which affords a new and pleasing quality to the flowers and greatly enhances its commercial value. Also this new variety has been observed and tested in northern California to be resistant to the common rose plant diseases such as blackspot, rust and mildew. Such observations have been made through several generations of the new variety, asexually propagated in commercial gardens and growing fields at Sebastopol, California, and at San Jacinto, California, in which areas the usual plant diseases are prevalent, and each generation of the new variety has been found to be consistently resistant to disease infection.

I claim:

A new and distinct variety of rose plant, as shown and described, characterized by its abundance of coral colored blossoms; its habit of continuously blooming; the uniquely scalloped margins of the flower petals; its winter hardiness; its resistance to diseases prevalent among roses; and its vigorous healthy growth.

No reference cited.